(12) United States Patent
Gross

(10) Patent No.: US 9,577,934 B2
(45) Date of Patent: Feb. 21, 2017

(54) OPTIMIZING PHYSIOLOGIC MONITORING BASED ON AVAILABLE BUT VARIABLE SIGNAL QUALITY

(75) Inventor: Brian Gross, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 772 days.

(21) Appl. No.: 12/918,822

(22) PCT Filed: Feb. 2, 2009

(86) PCT No.: PCT/IB2009/050422
§ 371 (c)(1),
(2), (4) Date: Aug. 23, 2010

(87) PCT Pub. No.: WO2009/107011
PCT Pub. Date: Sep. 3, 2009

(65) Prior Publication Data
US 2011/0002223 A1    Jan. 6, 2011

Related U.S. Application Data

(60) Provisional application No. 61/032,532, filed on Feb. 29, 2008.

(51) Int. Cl.
*H04L 12/26* (2006.01)
*H04L 12/801* (2013.01)
(Continued)

(52) U.S. Cl.
CPC ............. *H04L 47/10* (2013.01); *H04L 47/14* (2013.01); *H04L 47/25* (2013.01); *H04L 47/283* (2013.01)

(58) Field of Classification Search
CPC ....................................................... H04L 47/10
(Continued)

(56) References Cited

U.S. PATENT DOCUMENTS 6,364,834 B1 *   4/2002  Reuss et al. ................. 600/300
2001/0044823 A1 *  11/2001  Labounty et al. ............ 709/203
(Continued)

FOREIGN PATENT DOCUMENTS

GB          2410657 A       8/2005
JP          H11122300       4/1999
(Continued)

OTHER PUBLICATIONS

Rhue, T., et al.; Patient Monitoring in the Fast Lane: Case History; 2005; Health Management Technology; 26(12) abstract.
(Continued)

*Primary Examiner* — Christopher R Crompton

(57) ABSTRACT

When transmitting patient data over a hospital network, data types are prioritized into a data type hierarchy (26) that is employed to rank data types in order of criticality for transmission during periods of diminished signal quality. As signal quality decreases, less critical data types are omitted from transmission and stored to a gap data buffer for later transmission. As signal quality recovers, the less critical data types are restored to current data transmissions. Once all data types are restored during current transmission, previously omitted gap data is transmitted to fill in the gaps in a receiving device such as a network server to ensure that a complete data set is provided to the network and/or other devices coupled thereto.

20 Claims, 3 Drawing Sheets

(51) Int. Cl.
*H04L 12/825* (2013.01)
*H04L 12/841* (2013.01)

(58) Field of Classification Search
USPC .......................................................... 370/235
See application file for complete search history.

(56) References Cited

U.S. PATENT DOCUMENTS

| | | |
|---|---|---|
| 2004/0190528 A1 | 9/2004 | Dacosta |
| 2005/0002379 A1 | 1/2005 | Bye |
| 2005/0070315 A1* | 3/2005 | Rai et al. ...................... 455/466 |
| 2007/0109117 A1 | 5/2007 | Heitzmann et al. |
| 2008/0144586 A1* | 6/2008 | Kneckt et al. ................ 370/337 |
| 2011/0273287 A1* | 11/2011 | LaLonde et al. ........ 340/539.12 |

FOREIGN PATENT DOCUMENTS

| | | |
|---|---|---|
| JP | 2005509312 | 4/2005 |
| JP | 2007274443 | 10/2007 |
| WO | 0011841 A1 | 3/2000 |
| WO | 2007034387 A2 | 3/2007 |

OTHER PUBLICATIONS

Vergados, D. D.; Simulation and Modeling Bandwidth Control in Wireless Healthcare Information Systems; 2007; Simulation; 83(4)abstract.

\* cited by examiner

OPTIMIZING PHYSIOLOGIC MONITORING BASED ON AVAILABLE BUT VARIABLE SIGNAL QUALITY

CROSS REFERENCE TO RELATED APPLICATIONS

This application claims the benefit of U.S. provisional application Ser. No. 61/032,532 filed Feb. 29, 2008, which is incorporated herein by reference.

The present innovation finds particular application in patient monitoring, particularly involving physiologic monitoring over a healthcare network. However, it will be appreciated that the described technique may also find application in other information transmission and communication scenarios or techniques.

Utilization of contention-based wired and wireless networks provides a communication layer for a safe level of physiologic monitoring. Use of private networks and protected radio spectra support this effort. In many cases, wired bandwidth and wireless spectra (collectively referred as signal quality) are not available where applications need to run on existing and shared (e.g., not private) infrastructure. One drawback of conventional systems is that it is difficult to ensure that critical information is passed to the system when interference or contentious congestion limits the amount of available network bandwidth. In some applications the network is adaptive to support certain applications as higher traffic priorities over other applications where data latency and drop-out are not tolerated (Voice over IP as an example).

Often, the local area networks are employed in hospital networks, and the load on such networks varies significantly. When the load is high, or interferences exist, the available signal quality to any of the devices is low and the user perceived signal quality becomes poor. When the devices tries to upload more data than the network can carry, packets go undelivered, get lost, and the like. This creates gaps in the monitored data and can result in missing physiologic information necessary to feed alerting algorithms or reconstruct data in review applications. When a device fails to receive the required confirmations (e.g., an acknowledgement or "ACK") and when some number of packets has been unsuccessfully received or delayed, the devices consider the connection lost and may try to reestablish a new connection. This causes breaks and gaps in the data and in the monitoring. This is particularly troubling when physiologic waveforms data becomes gap data.

Conventional physiologic monitoring systems expect a fixed bandwidth over which to pass required application data. When interferers are present that reduce the available signal quality, essential performance is typically not met and the user is alerted to the loss of monitoring. Again, such systems typically shut down the connection completely and then re-establish a connection once adequate connection quality is present.

The present application provides new and improved physiologic monitoring systems and methods, which overcome the above-referenced problems and others.

In accordance with one aspect, a network communication optimization system includes a transceiver that transmits and receives data over a network, and a signal quality analyzer that detects network congestion and latency as a function of actual data delivery and application-based latency measurement. The system further includes a transmission controller that selectively reduces current data types to be transmitted by the transceiver during periods of diminished signal quality according to a predetermined data type hierarchy, and a buffer that stores gap data omitted during reduced data transmission.

In accordance with another aspect, a method of optimizing data transmission in response to network congestion includes continuously monitoring signal quality availability on a network, and transmitting all current data when signal quality availability is above a first predetermined threshold. The method further includes incrementally reducing current data transmission according to a predetermined data type hierarchy to be successively omitted when signal quality availability drops below each of N successive predetermined thresholds, wherein N is a positive number and includes the first predetermined threshold, and buffering omitted data (or other data acquired when there is no network connectivity), for later transmission. Additionally, the method includes incrementally increasing current data transmission according to the predetermined data type hierarchy of when signal quality availability rises above any of the N successive predetermined thresholds, including the first predetermined threshold, and transmitting the omitted data when signal quality availability returns to a level above the first predetermined threshold.

One advantage is that communication links are not completely terminated during reduced bandwidth periods.

Another advantage resides in ensuring higher priority data, such as patient monitoring alarms are transmitted, even during periods of severely diminished bandwidth.

Another advantage is that the application adapts to the ability to get the data to the target client and keeps track of what is missing so all the data will eventually get to the system repository.

Another advantage is that there are no special network considerations or prior commitment to dedicated bandwidth needed to support the adaptive data algorithm.

Still further advantages of the subject innovation will be appreciated by those of ordinary skill in the art upon reading and understanding the following detailed description.

The innovation may take form in various components and arrangements of components, and in various steps and arrangements of steps. The drawings are only for purposes of illustrating various aspects and are not to be construed as limiting the invention.

Systems and methods are described herein that detect available signal quality variations, automatically throttle application access and communication content, and provide a mechanism for the exchange of data once the expected network signal quality resumes. These systems and methods have specific relevance to medical device and health information systems for wired and wireless medical LAN applications, and have broader application to other areas where critical data throughput is impaired by variable signal quality (wired and wireless bandwidth) infrastructure.

Figure 1:
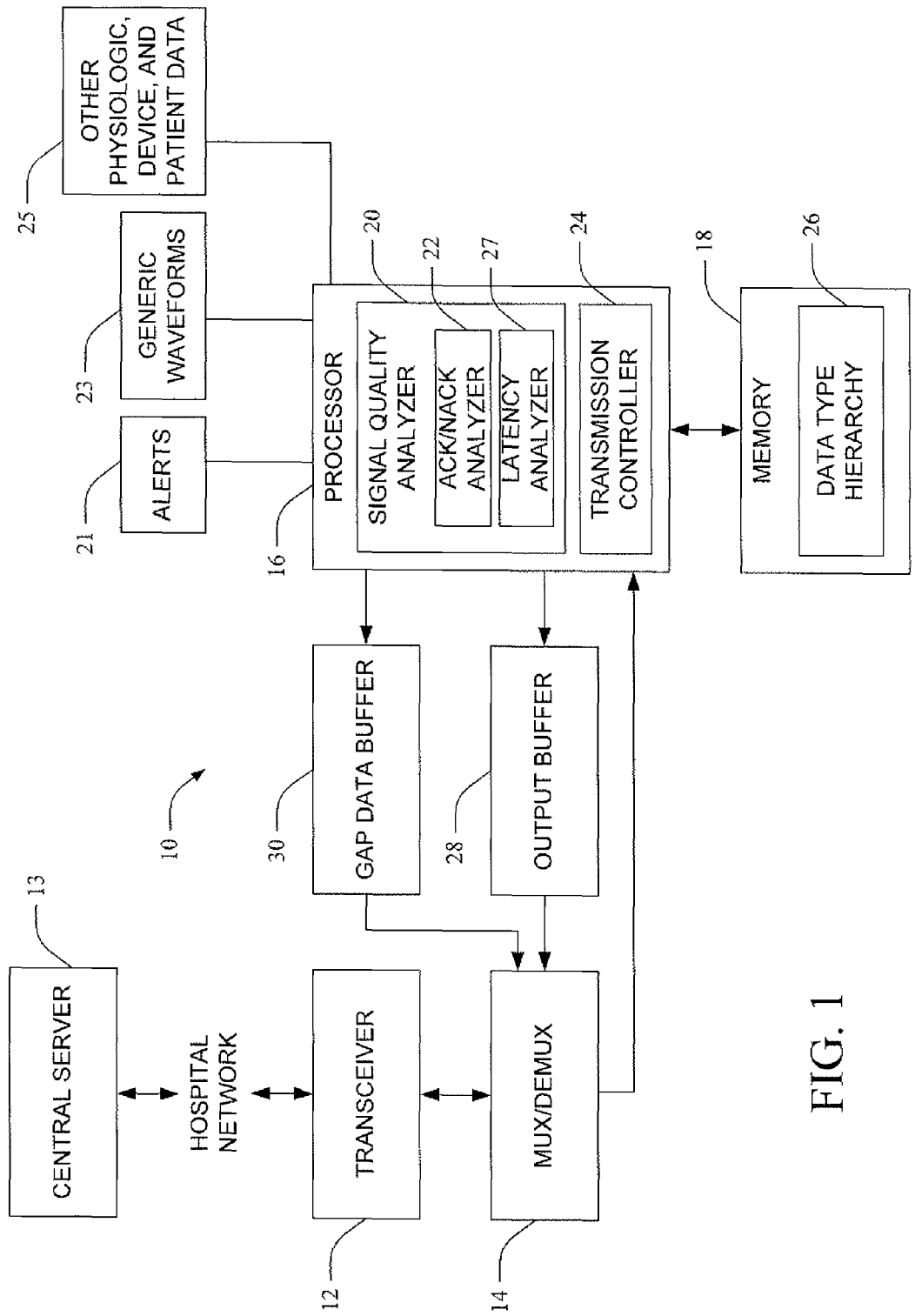
FIG. 1 illustrates a data transmission optimization system for utilizing an adaptable data communication process whereby applications throttle data between devices and the system in cases where network congestion or latency is present.

FIG. 1 illustrates a data transmission optimization system 10 for utilizing an adaptable data acquisition process whereby applications throttle data and data types between devices and the system in cases where network congestion is present. This unique approach ensures that expected performance levels are maintained and further provide a method where gap data (data unknown to the network) is cached by the device and transmitted at a later time when sufficient bandwidth is present.

The system 10 includes a transceiver 12 that transmits data to and receives data from a hospital network, such as a hospital network comprising a plurality of patient monitors, workstations, servers including a central server 13, non-medical devices, applications, and the like. The transceiver is coupled to a multiplexer/demultiplexer (MUX/DEMUX) 14 that multiplexes and/or modulates outgoing data and demultiplexes and/or demodulates incoming data for processing by a processor 16. The processor is coupled to a memory 18 that stores incoming data (e.g., pre- and post-processed data), data to be transmitted to the network, algorithms and/or routines for processing data, evaluating signal quality, adjusting data transmission volume as a function of available signal quality, and the like.

The processor includes a signal quality analyzer 20 that detects and quantifies network congestion. The signal quality analyzer includes an ACK/NACK analyzer 22 that quantifies a ratio of transmitted data packets for which acknowledgements have been received (e.g., indicating successful receipt by the network server 13 and/or other recipient devices) versus transmitted packets for which no acknowledgement has been received. This ratio is employed by the signal quality analyzer to infer that network congestion is present and that available signal quality is therefore diminished. The signal quality analyzer also includes an application-based latency analyzer 27 so data that arrives, but arrives late can be detected by a receiving application and included in the determination of adequate system throughput. In one embodiment, the latency analyzer analyzes a data reading number for a given data type, wherein the data reading number is a data packet encoded with a high resolution clock counter via which the latency analyzer measures latency. In another embodiment, the data itself is used to determine throughput and latency, permitting data measurement to be made in transmission modes such as transmission control protocol (TCP), user datagram protocol (UDP) or any other suitable transmission mode. Yet another approach relates to reserving bandwidth for pre-specified applications, which facilitates employing the systems and methods described herein on any communication network without reliance on quality of service.

The signal quality analyzer 20 can optionally perform period or continuous review of historical signal quality data for comparison to the current signal quality data in view of the predetermined signal quality thresholds delineated in the data type hierarchy. This historical quality data can additionally be used as a trigger to notify clinical users to the reason of limited data availability in the medical application, as well as the system administrator to potential problems in the network. A transmission controller 24 then executes a routine (e.g., stored in the memory) for omitting predefined data types form a transmission signal to reduce data transmission volume during the period of diminished signal quality or increased latency. The order in which data types are omitted as signal quality decreases is a function of a predefined data type hierarchy 26 stored in the memory 18.

The processor 16 is additionally coupled to a plurality of physiologic sensors and physiologic waveforms such as generic waveforms (e.g., electrocardiogram and the like), an alert generator 21, and/or one or more other types of physiologic, device, and/or patient data 25 that describe patient parameters (e.g., heart rate, blood pressure, respiration rate, $SpO_2$, or any other parameter that can be monitored or used in conjunction with monitoring for clinical decisions and alerting including patient demographics and reports). These devices provide the data to be output from the processor 16 to the hospital network.

Data to be transmitted is passed from the processor through an output buffer 28 to the MUX for modulation and/or multiplexing before being transmitted to the network by the transceiver. During periods of reduced data transmission (e.g., due to diminished signal quality as detected by the signal quality analyzer), the transmission controller omits one or more data types as prescribed by the data type hierarchy. Omitted data is cached to a gap data buffer 30 that stores the gap data until sufficient signal quality is available for transmission.

In one embodiment, the signal quality analyzer continuously monitors signal quality availability and delivery latency, and when the ACK/NACK analyzer does not detect any NACKs (e.g., for a prescribed time period or number of data packets), or appreciable delivery delay (latency) the transmission controller adds omitted data types back to a current transmission as prescribed by the hierarchy (e.g., in reverse order relative to the order of omission). Once signal quality availability has increased to a level at which all data types are being transmitted again, the processor begins to transmit gap data (e.g., data previously omitted during reduced transmission and low signal quality availability). Cached gap data is retrieved from the gap data buffer 30 and passed upstream through the MUX to the transceiver for transmission to the network.

According to another embodiment, the transmission controller 24 holds data packets in the output buffer 28 until confirmation of receipt (e.g., an ACK) is received. However, when confirmations are not received (e.g., no acknowledgement, or "NACK"), or are received too late (e.g., latency) for the data type, the data is moved to the gap data buffer 30. The signal quality analyzer, in conjunction with the ACK/NACK and latency analyzer, determines how much signal is available based on the number of packets which are not being successfully transmitted. When less than full bandwidth is available, the transmission controller not only causes some packets to be stored, but also changes the content of the packets. For example, if any bandwidth is available, alerts or packets containing the alerts will be transmitted. If there is a little more signal quality available, the ECG signals will be sent, etc. If the system is operating on reduced signal quality but no packets are going undelivered, then the transmission controller begins increasing the amount of information that is being transmitted. Once sufficient signal quality is detected or reestablished to transmit all of the current data, the transmission controller attempts to obtain even more signal quality in order to transmit the previously omitted gap data from storage in the gap data buffer 28. In this manner, the gaps in the data at a destination location (e.g., a network server, workstation, etc.) are filled in to provide a complete data history. Thus, the system 10 mitigates typical and unexpected interruptions to the quality of service encountered in shared network environments, and ensures that expected data is presented to the network at a later time when increased signal quality availability is detected.

Figure 2:
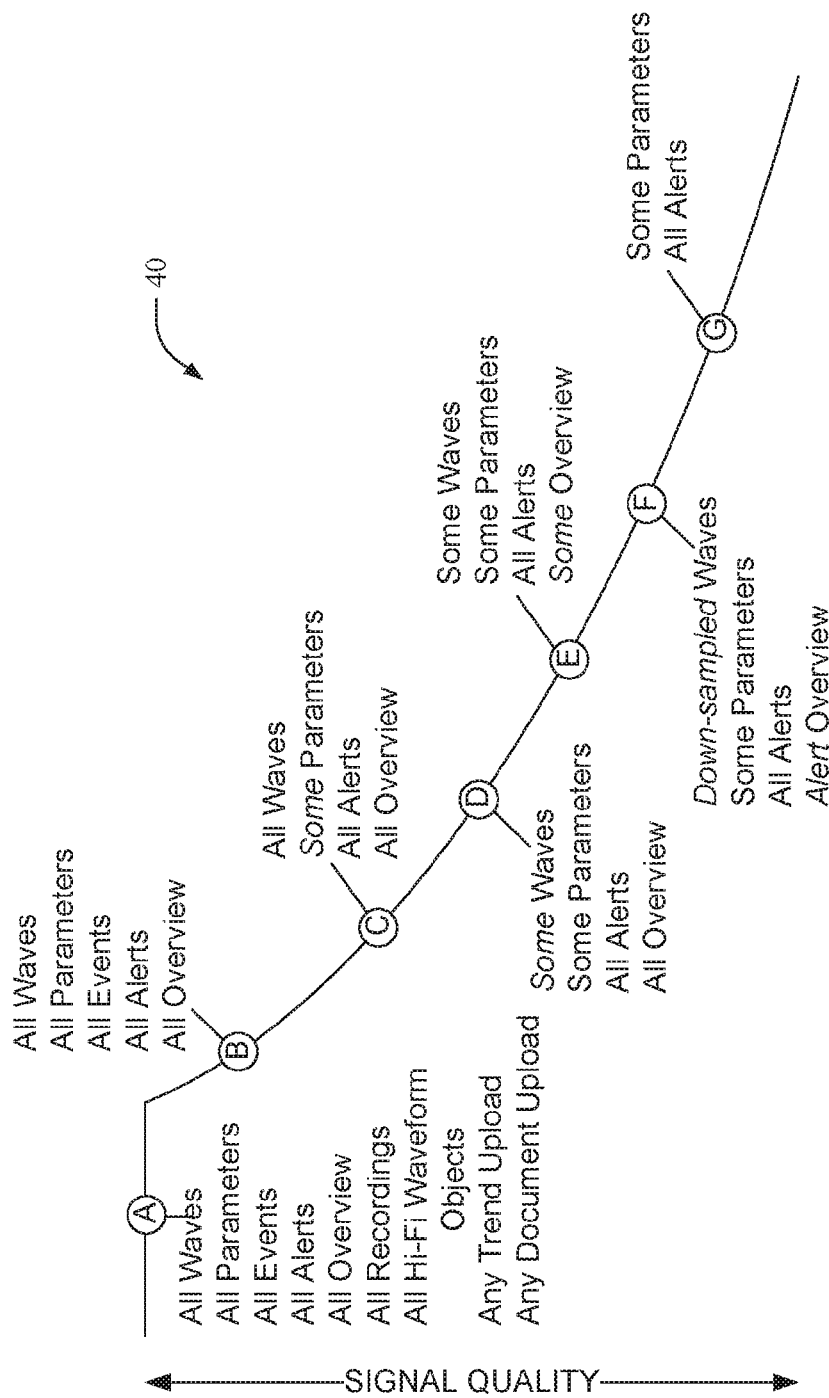
FIG. 2 is an illustration of a graph showing examples of data type hierarchical relationships as a function of signal quality availability.

FIG. 2 is an illustration of a graph 40 showing examples of data type hierarchical relationships as a function of signal quality availability. In one embodiment, data communication is performed with knowledge of current throughput for all devices with which a network server or given device is communicating. In cases where communication is impaired due to interference, congestion, or failures, resulting in a limited but extant connection, the devices on the network have a prearranged agreement on what data to stop sending and in what priority to ensure that a certain minimum performance and vigilant patient monitoring is maintained.

According to the figure, a plurality of points, A-G, are illustrated at different successive levels of decreased bandwidth availability. At point A, full bandwidth is available, and thus all current data is transmitted. For instance, complete data may include, without being limited to, an N-wave physiologic signal (e.g., ECG, heart rate, $SpO_2$, respiration rate, invasive blood pressure, pressure and flow patterns, etc.), where N is an integer, all patient parameters, events, alarms, overview data (physiologic data sent from one bed to another), recordings, high fidelity wave snippet data, any available trend uploads, any available document uploads, etc. At point B, where signal quality is somewhat diminished, current data transmission is reduced to the N waveforms, parameter, event, alarm, and overview data. Omitted data is cached for transmission when the signal quality availability increases to the level shown at point A. At point C, signal quality is further diminished, and current data transmission is reduced further, to the exclusion of event data and some of the parameter data. At point D, some of the N waveforms are omitted. Some of the overview data is omitted at point E. At point F, waveforms are down-sampled to further reduce signal quality requirements, and overview data is reduced to include only alert and overview information. At point G, only alerts and some of the parameter information is transmitted, since signal quality is severely limited. At each point B-G, any data (e.g., listed in the data set of point A) that is omitted due to reduced signal quality is cached to the gap data buffer for later transmission.

That is, in "full signal quality" mode, the system is able to receive a superset of physiological waveforms, parameters, alerts, and other application requests. As the signal quality decreases, the system suppresses features and/or locally caches data until the "full" communication signal quality is returned. If further reduction in signal quality is detected, background uploads (gap data and/or print requests) are suspended until communications recover and signal quality availability increases.

If still further reductions are detected, reductions on the total physiological data set are made (and omitted data is marked as "gap" data) until signal quality recovery is detected. The system 10 reduces to the minimal number of waveforms, parameters and alerts needed to enable patient monitoring. If further reduction is detected, the system sends down-sampled wave data at a lower bit resolution and sends only the primary wave (e.g., ECG), until recovery. In minimal data throughput, the system sends only alerting information and periodic numeric data until recovery. During recovery, the system first restores full fidelity real-time data from all subscribers, then prioritizes cached or gap data with the sending devices.

The foregoing examples illustrate a data type hierarchy that may be employed in conjunction with the systems and methods described herein. However, it is to be appreciated that the data type hierarchy is not limited to the above-described patient-monitoring data types, but rather may include any classes or types of data (e.g., data from interfaced devices such as ventilators, intravenous medication therapy and feeding pumps, etc.) transmitted over a network in which the systems and or methods described herein are employed. Moreover, the signal quality availability levels need not be evenly or linearly spaced over a total amount of signal quality, but rather may be defined or arranged in any desired manner.

Figure 3:
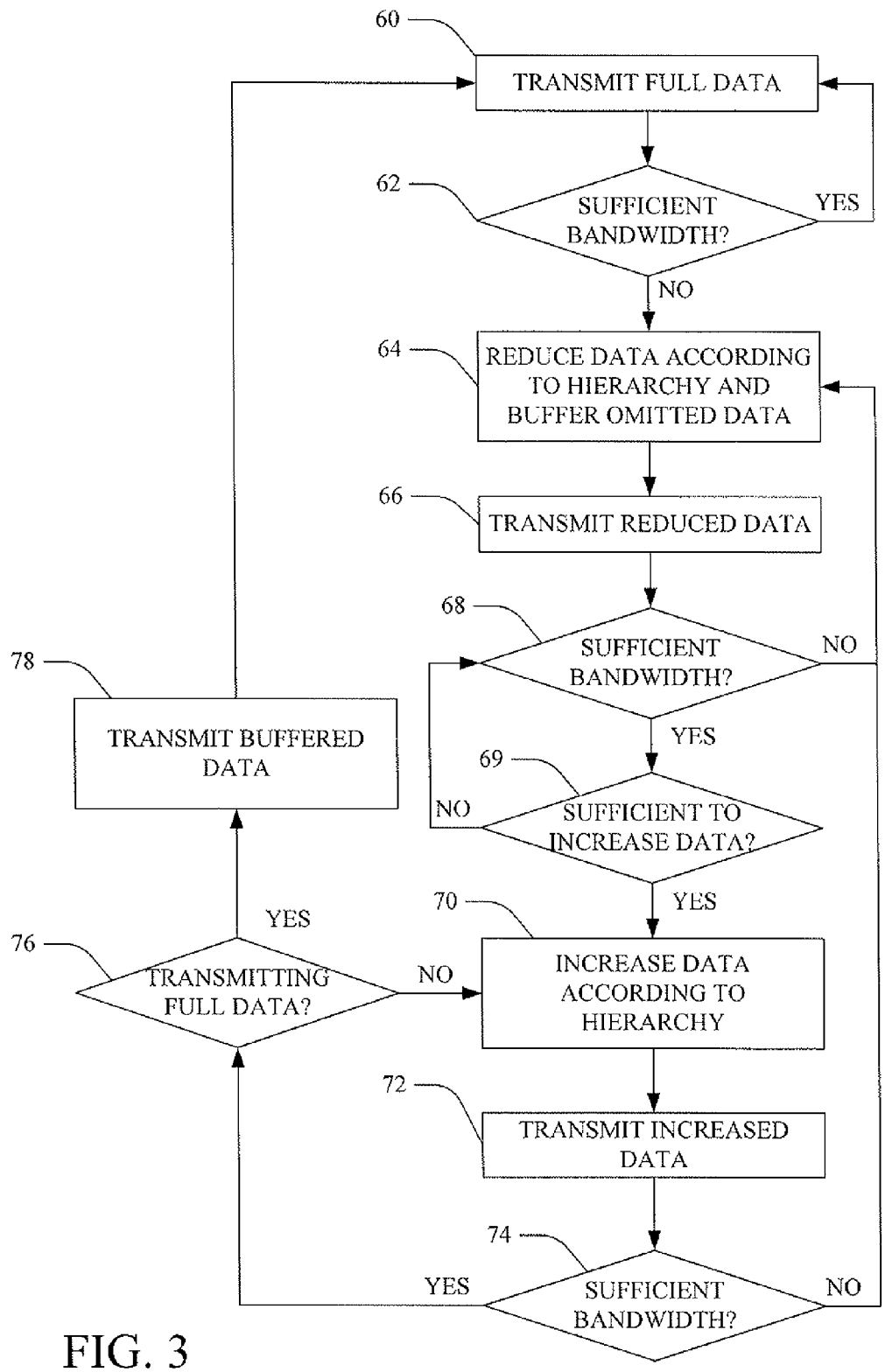
FIG. 3 illustrates a flow chart diagram of a method of selectively adjusting data transmission as a function of signal quality availability, in accordance with various aspects described herein.

FIG. 3 illustrates a flow chart diagram of a method of selectively adjusting data transmission as a function of signal quality availability, in accordance with various aspects described herein. At 60, a complete or full set of current data is transmitted from a device coupled to a network. At 62, a available signal quality is assessed. Although depicted as various steps in the method, it will be appreciated that signal quality availability assessment and/or detection is performed continuously as a function of ACKs received by the device for transmitted data packets, as described with regard to FIG. 1. If sufficient signal quality is available (e.g., the device has received ACKs for all or at least a predetermined percentage of all transmitted data packets, and data latency is below the predetermined level for the data types, then the method reverts to 60 and full data transmission is continued.

If sufficient signal quality is not available, (e.g., a predetermined percentage of transmitted data packets receive NACKs, or do not receive ACKs), or if the data latency is above the predetermined level, then at 64, data transmission is reduced according to priority indicated by the data type hierarchy, and one or more data types are omitted from the current transmission while the omitted data is cached in a designated buffer. At 66, the reduced data set is transmitted. Signal quality availability is evaluated with regard to latency and ACKs/NACKs for the reduced data transmission, at 68. If signal quality is not sufficient for transmission of the reduced data set, then the method reverts to 64, where further transmission reduction is performed.

If, at 68, it is determined that sufficient bandwidth is available for the current transmission volume, then at 69 a determination is made regarding whether sufficient signal quality is present to increase data transmission volume. If not, then the method reverts to 68 and data transmission continues at the current reduced volume. If so, then at 70 transmission data is increased (e.g., by including previously omitted data types) according to the data type hierarchy. The increased data set is transmitted at 72. Bandwidth availability is reassessed at 74 based on the increased data transmission. If bandwidth is not sufficient, then the method reverts to 64 for data reduction according to the data type hierarchy.

If signal quality is sufficient at 74, then at 76 a determination is made regarding whether a complete or full data set is currently being transmitted. If not, then the method reverts to 70 for further increase of the data types included in transmission, as prescribed by the data type hierarchy. If full data is being transmitted, then at 78, buffered gap data (e.g., previously omitted data stored to the dedicated buffer during reduced data transmission) is transmitted, in addition to transmission of the complete current data set.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

The invention claimed is:

1. A network communication optimization system, including:
   a transceiver that transmits and receives data over a network;

a signal quality analyzer that detects network congestion and latency as a function of actual data delivery and application-based latency measurement;
a transmission controller that selectively reduces current data types to be transmitted by the transceiver during periods of diminished signal quality according to a predetermined data type hierarchy;
a buffer that stores gap data omitted during reduced data transmission;
wherein the transmission controller suspends transmission of buffered gap data before reducing current data transmission in response to detected network congestion or latency;
wherein the data type hierarchy includes, in order of priority from highest to lowest where lower priority data types are omitted from transmission before higher priority data types, the following groups of data types:
alert data;
one or more of:
alert overview data and down-sampled waveform data; and
overview data;
waveform data;
parameter data and event data; and
trend upload data, local cache data, and document upload data.

2. The system according to claim 1, employed in a hospital network, and further including a central server that receives data from the transceiver derived from one or more of at least one physiologic sensor and at least one device capable of providing device data or patient physiologic data.

3. The system according to claim 2, further including an acknowledgement analyzer that evaluate acknowledgements received for transmitted data packets and a latency analyzer that determines a level of network congestion or latency.

4. The system according to claim 2, wherein the transmission controller varies the amount of current data transmitted by the transceiver from full data transmission during periods of no or low congestion down to transmission of alerts during periods of high congestion.

5. The system according to claim 4, wherein the signal quality analyzer continuously evaluates signal quality availability, and the transmission controller increases or decreases current data transmission as a function of current signal quality availability.

6. The system according to claim 5, wherein the transmission controller initiates transmission of buffered gap data when signal quality availability increases to a level sufficient for full current data transmission to fill in data gaps caused by data omission during reduced data transmission.

7. The system according to claim 2, wherein the data type hierarchy includes a plurality of data types, of which the "alert" data type has a highest priority relative to other data types to ensure that alerts are transmitted even during periods of high network congestion.

8. The system according to claim 7, wherein alert-type data includes a minimum number of waveforms, alerts, and parameters for monitoring a patient.

9. A network communication optimization system, including:
a transceiver transmits and receives data over a network;
a signal quality analyzer that detects network congestion and latency as a function of actual data delivery and application-based latency measurement;
a transmission controller that selectively reduces current data types to be transmitted by the transceiver during periods of diminished signal quality according to a predetermined data type hierarchy;
a buffer that stores gap data omitted during reduced data transmission;
wherein the transmission controller suspends transmission of buffered gap data before reducing current data transmission in response to detected network congestion or latency;
wherein the system is employed in a hospital network, and further including a central server that receives data from the transceiver derived from one or more physiologic sensors or/and devices capable in providing device data or patient physiologic data;
wherein the data type hierarchy includes a plurality of data types, of which the "alert" data type has a highest priority relative to other data types to ensure that alerts are transmitted even during periods of high network congestion; and
wherein the data type hierarchy includes, in order of priority from highest to lowest where lower priority data types are omitted from transmission before higher priority data types, the following groups of data types:
alert data;
alert overview data and down-sampled waveform data;
overview data;
waveform data;
parameter data and event data; and
trend upload data, local cache data, and document upload data.

10. A method of varying data transmission in response to network congestion using the system of claim 1, including:
continuously monitoring signal quality availability on the network;
transmitting all current data types when signal quality availability is above a first predetermined threshold;
incrementally reducing current data type transmission according to the predetermined data hierarchy to be omitted when signal quality availability drops below each of N successive predetermined thresholds, wherein N is a positive number and includes the first predetermined threshold;
buffering omitted data for later transmission;
incrementally increasing current data transmission according to the predetermined data type hierarchy when signal quality availability rises above any of the N successive predetermined thresholds, including the first predetermined threshold; and
transmitting the omitted data when signal quality availability returns to a level above the first predetermined threshold.

11. A method of optimizing data transmission in response to network congestion, including:
continuously monitoring signal quality availability on a network;
transmitting all current data when signal quality availability is above a first predetermined threshold;
incrementally reducing current data transmission according to a predetermined data type hierarchy to be successively omitted when signal quality availability drops below each of N successive predetermined thresholds, wherein N is a positive number and includes the first predetermined threshold;
buffering omitted data for later transmission;
suspending transmission of buffered gap data before reducing current data transmission in response to detected network congestion or latency;

incrementally increasing current data transmission according to the predetermined data type hierarchy of when signal quality availability rises above any of the N successive predetermined thresholds, including the first predetermined threshold; and transmitting the omitted data when signal quality availability returns to a level above the first predetermined threshold;

wherein the data type hierarchy includes, in order of priority from highest to lowest where lower priority data types are omitted from transmission before higher priority data types, the following groups of data types:

alert data; and one or more of:

alert overview data and down-sampled waveform data; and overview data;

waveform data;

parameter data and event data;

trend upload data, local cache data, and document upload data.

12. The method according to claim 11, employed in a hospital network that receives the transmitted data, which comprises information collected by one or more sensors, patient monitors, or physiological data sending device.

13. The method according to claim 12, further comprising analyzing acknowledgement and latency information for transmitted data packets to determine signal quality availability.

14. The method of claim 11, wherein only patient monitoring alert information is transmitted when signal quality availability is below the Nth predetermined threshold.

15. The method according to claim 14, wherein the alert information includes an alarm and a waveform for a monitored parameter causing the alarm.

16. The method according to claim 11, further comprising determining whether signal quality availability has been restored to a level at or above the first predetermined threshold and transmitting a full current data set when signal quality availability has been restored to a level at or above the first predetermined threshold.

17. The method according to claim 16, further comprising transmitting buffered gap data once full current data transmission is reinstated and acknowledgements are received for a predefined percentage of current data packets.

18. The method according to claim 17, further comprising terminating transmission of gap data if acknowledgements for transmitted current data packets drop below a predefined acceptable threshold level.

19. A non-transitory computer readable medium having stored thereon computer-executable instructions for performing the method of claim 11.

20. An apparatus for optimizing data transmission, including:

a processor configured to perform the method of claim 11.

* * * * *